US006849088B2

(12) United States Patent
Dehdashtian et al.

(10) Patent No.: US 6,849,088 B2
(45) Date of Patent: Feb. 1, 2005

(54) AORTO UNI-ILIAC GRAFT (75) Inventors: Mark Dehdashtian, Costa Mesa, CA (US); Teodoro S. Jimenez, Jr., Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 20 days.

(21) Appl. No.: 10/055,787

(22) Filed: Nov. 7, 2001

(65) Prior Publication Data

US 2003/0033002 A1 Feb. 13, 2003

Related U.S. Application Data (63) Continuation-in-part of application No. 09/204,699, filed on Dec. 3, 1998, now Pat. No. 6,368,345, which is a continuation-in-part of application No. 09/163,580, filed on Sep. 30, 1998, now abandoned.

(51) Int. Cl.[7] .................................................. A61F 2/06
(52) U.S. Cl. ..................................... 623/1.36; 623/1.13
(58) Field of Search .............................. 623/1.13, 1.14, 623/1.15, 1.23, 1.36

(56) References Cited

U.S. PATENT DOCUMENTS

| 5,064,435 | A | 11/1991 | Porter |
| 5,122,154 | A | 6/1992 | Rhodes |
| 5,180,362 | A | 1/1993 | Worst |
| 5,397,345 | A | 3/1995 | Lazarus |
| 5,443,497 | A | 8/1995 | Venbrux |
| 5,489,295 | A | 2/1996 | Piplani et al. |
| 5,507,769 | A | 4/1996 | Marin et al. |
| 5,522,880 | A | 6/1996 | Barone et al. |
| 5,562,726 | A | 10/1996 | Chuter |
| 5,562,728 | A | 10/1996 | Lazarus et al. |
| 5,575,817 | A | 11/1996 | Martin |
| 5,609,605 | A | 3/1997 | Marshall et al. |

(List continued on next page.)

FOREIGN PATENT DOCUMENTS

| EP | 0686379 | 6/1996 |
| EP | 0808614 A2 | 11/1997 |
| FR | 2 748 197 | 5/1996 |
| WO | WO 95/08966 | 4/1995 |
| WO | WO 96/11648 | 4/1996 |
| WO | WO 97/17910 | 5/1997 |
| WO | WO 97/17911 | 5/1997 |
| WO | WO 97/26936 | 7/1997 |
| WO | WO 97/26938 | 7/1997 |
| WO | WO 99/01073 | 1/1999 |
| WO | WO 99/32050 | 7/1999 |
| WO | WO 99/37242 | 7/1999 |
| WO | WO 01/30270 A2 | 5/2001 |

OTHER PUBLICATIONS

Marin, Michael L., et al, "Initial Experience with Transluminally placed Endovascular Grafts for the Treatement of Complex Vascular Lesions," Annals of Surgery, vol. 222, No. 4, pp 449–469, 1995, Lippincott–Raven Publishers.

(List continued on next page.)

Primary Examiner—Cary E. O'Connor
(74) Attorney, Agent, or Firm—Edwards Lifesciences (57) ABSTRACT A generally tubular intraluminal vascular graft having a linear shape that may be radially expanded from a compressed state to an expanded state within a body vessel is disclosed. The graft includes a plurality of stent portions which take the form of undulating filaments extending circumferentially along the tubular body and forming a generally ring-shaped configuration. The graft may further be equipped with a plurality of specifically-configured engagement members disposed on the outer surface of the graft which are configured to frictionally engage an inner wall of a vessel so as to inhibit longitudinal movement of the tubular body without piercing the vessel wall.

29 Claims, 6 Drawing Sheets

U.S. PATENT DOCUMENTS

| | | |
|---|---|---|
| 5,609,627 A | 3/1997 | Goicoechea et al. |
| 5,628,783 A | 5/1997 | Quiachon et al. |
| 5,628,788 A | 5/1997 | Pinchuk |
| 5,632,772 A | 5/1997 | Alcime et al. |
| 5,662,675 A | 9/1997 | Polanskyj Stockert et al. |
| 5,665,117 A | 9/1997 | Rhodes |
| 5,667,523 A | 9/1997 | Bynon et al. |
| 5,676,696 A | 10/1997 | Marcade |
| 5,676,697 A | 10/1997 | McDonald |
| 5,683,449 A | 11/1997 | Marcade |
| 5,683,453 A | 11/1997 | Palmaz |
| 5,693,088 A | 12/1997 | Lazarus |
| 5,713,917 A | 2/1998 | Leonhardt et al. |
| 5,728,131 A | 3/1998 | Frantzen et al. |
| 5,755,771 A | 5/1998 | Penn et al. |
| 5,769,887 A | 6/1998 | Brown et al. |
| 5,782,904 A * | 7/1998 | White et al. |
| 5,797,949 A | 8/1998 | Parodi |
| 5,824,037 A * | 10/1998 | Fogarty et al. |
| 5,824,039 A | 10/1998 | Piplani et al. |
| 5,824,040 A | 10/1998 | Cox et al. |
| 5,824,042 A | 10/1998 | Lombardi et al. |
| 5,824,055 A | 10/1998 | Spiridigliozzi et al. |
| 5,843,160 A | 12/1998 | Rhodes |
| 5,871,536 A | 2/1999 | Lazarus |
| 5,906,641 A | 5/1999 | Thompson et al. |
| 5,968,068 A | 10/1999 | Dehdashtian et al. |
| 6,030,415 A | 2/2000 | Chuter |
| 6,071,307 A | 6/2000 | Rhee et al. |
| 6,099,558 A | 8/2000 | White et al. |
| 6,102,938 A | 8/2000 | Evans et al. |
| 6,193,745 B1 | 2/2001 | Fogarty et al. |
| 6,203,568 B1 | 3/2001 | Lombardi et al. |
| 6,287,330 B1 | 9/2001 | Johansson et al. |
| 2002/0123790 A1 * | 9/2002 | White et al. ............... 623/1.14 |

OTHER PUBLICATIONS

May, James et al., "Treatment of Complex Abdominal Aortic Aneurysms by a Combination of Endoluminal and Extraluminal Aortofemoral Grafts." Journal of Vascular Surgery, vol. 19, No. 4, pp 924–933, 1994.

May, James, et al. "Endoluminal Repair of Atypical Dissecting Aneurysm of Descending Thoracic Aorta and Fusiform Aneurysm of the Abdominal Aorta." Journal of Vascular Surgery, vol. 22, No. 2, pp 167–172, 1995.

Parodi, Juan Carlos. "Endovascular Repair of Abdominal Aortic Aneurysms and other Arterial Lesions." Journal of Vascular Surgery, vol. 21 No. 4, pp 549–557, 1995.

Sanada, J. M.D., "Clinical Application of a Curved Nitinol Stent–Graft for Thoracic Aortic Aneurysms." Journal of Endovascular Therapy, vol. 10, Issue 1, pp 20–28, Feb. 2003.

White, Geoffrey H., et al, "Three–Year Experience with the White–Yu Endovascular GAD Graft for Transluminal Repair of Aortic and lilac Aneurysms." Journal of Endovascular Surgery, vol. 4, pp 124–146, 1997.

* cited by examiner

AORTO UNI-ILIAC GRAFT

CROSS REFERENCE TO RELATED APPLICATIONS

The instant application for U.S. Letters Patent is a continuation-in-part application of U.S. patent application Ser. No. 09/204,699 filed Dec. 3, 1998, now U.S. Pat. No. 6,368,345 issued on Apr. 9, 2002, which is a Continuation-in-Part of U.S. patent application Ser. No. 09/163,580 filed Sep. 30, 1998 (abandoned), both of which are specifically incorporated herein by reference.

The instant application for U.S. Letters Patent also claims priority to Australian provisional Patent Application No. PQ 3029, filed Sep. 23, 1999, and to World Intellectual Property Organization Patent Application No. PCT/US00/26239, both of which are specifically incorporated herein by reference.

BACKGROUND OF THE INVENTION

1. Field of the Invention

The present invention relates to an intraluminal device for use in the treatment of aneurysmal or stenotic disease. Particularly, the present invention relates to endovascular emplacement of structures designed to enhance a patient's vasculature, particularly those areas of a patient's vasculature that do not have sizeable branches extending therefrom.

2. Discussion of the Related Art

An aneurysm is a ballooning of the wall of an artery resulting from weakening due to disease or other condition. Left untreated, the aneurysm may rupture, resulting in severe loss of blood and potentially death. An aneurysm in the abdominal aorta is the most common form of arterial aneurysm. The abdominal aorta, which extends downward from the heart in front of and parallel to the spine, through the thorax and abdomen, and generally branches off in a plurality of side vessels, connects the ascending aorta at the heart and to the circulatory system of the trunk and lower body. Branched vessels of the aorta supply the two kidneys via oppositely-directed renal arteries. Below the renal arteries in typical human anatomy, the abdominal aorta continues to about the level of the fourth lumbar vertebrae and divides at a Y-junction into the left and right iliac arteries, which supply blood to the lower extremities.

A common location for an aortic aneurysm is in the section of aorta between the renal and iliac arteries. Without rapid surgical intervention, a rupture of the abdominal aorta is commonly fatal because of the high volume of blood flow within the aorta. Conventional surgical intervention involves penetrating the abdominal wall to the location of the aneurysm to reinforce or replace the diseased section of the aorta. Typically, a prosthetic tube graft replaces the area of, or proximal and distal zones abutting, a potential rupture portion of the aorta. Unfortunately, conventional surgical intervention has resulted in substantial morbidity rates, and at the very least a protracted recovery period. Likewise, cost and other constraints militate for a longstanding need for endovascular intervention.

In recent years, methods and devices have been developed to treat an aortic aneurysm without opening up the abdominal wall. These new techniques typically involve a catheter-carried tubular graft delivered upward from the femoral artery through the iliac artery and into the region of the aneurysm. The graft normally includes a tubular graft body supported by an expandable stent, either self-expanding or balloon-expanding. The balloon-expanding type of stent naturally requires an expansion balloon, while the self-expanding type is simply deployed from the end of a tubular sheath. Emplacement issues impact upon both known techniques.

Endovascular grafts and stented grafts are generally known to be useful in several distinct configurations. For example, it is known to use intraluminal grafts and stents of various designs for the treatment of aneurysms such as aortic aneurysms, and occlusive diseases affecting the vasculature or other vessels comprising, inter alia, the hepto-biliary and genito-urinary tracts (which are all hereinafter "vessels"). It is known to form such an intraluminal device of a sleeve in which is disposed a plurality of wire stents (see Balko A. et al (1986) *Transfemoral Placement of Intraluminal Polyurethane Prosthesis for Abdominal Aortic Aneurysms*, 40 Journal of Surgical Research 305–309; Mirich D. Et al. (1989) *Percutaneously Placed Endovascular Grafts for Aortic Aneurysms: Feasibility Study* 170(3) Radiology 1033–1037).

In the past, such devices have commonly be used in the treatment of, or to exclude aneurysms, see, e.g., U.S. Pat. Nos.: 5,782,904; 5,986,068; 6,013,092; 6,024,729; 6,045,557; 6,071,307; 6,099,558; 6,106,540; 6,110,191; 6,143,014; 6,231,563; and 6,278,079, each of which is licensed or assigned to and may be available from Edwards Lifesciences LLC (Orange County, Calif.), the instant assignee, and each of which is expressly incorporated herein by reference.

Whatever the purpose for which an intraluminal device is being used, it has the capacity to be inserted percutaneously through a distal (or proximal) and connecting vessel to that in which the device is to be used. For example, it may be inserted through the femoral artery in a catheter, where the device is intended to be used in the treatment of a lesion within the aorta. Upon release of the device from the catheter it may expand or be expanded to a desirable size, and may extend above and below the lesion thereby bridging the lesion. This method of inserting the device into the body of a patient is applicable where the invention is used in the treatment of aneurysmal disease or stenotic disease.

There are several potential problems associated with most known intraluminal devices. For instance, conventional grafts are not designed to follow the natural curvature of some vessels and may, therefore, kink if required to bridge a section of vessel that has a natural curvature. Alternatively, some graft candidates have atypical vasculature. For example, some candidates have an aorta that does not funnel blood into two iliacs. This may be caused either by a complete occlusion in one iliac, or by a variation in an individual patient's vasculature. In the past, a bifurcated graft having one leg sewn shut or otherwise removed has been used to treat aneurysms or stenotic disease in these and other non-branching vessels. However, such alteration of the bifurcated graft generally does not provide as even a flow path as is desired. Additionally, this requires an additional step on the part of the administering physician. Furthermore, it may be difficult to use such a bifurcated graft as a conversion graft, or to supplement a failed or failing graft.

Despite much work in this highly competitive field, there is still a need for a graft that is specifically designed to be used with generally straight vasculature or vessels.

SUMMARY OF THE INVENTION

In a first aspect, the present invention consists in an intraluminal device comprising a tubular body having a length, a first end and a second end, wherein the tubular body has a pre-determined, generally linear shape, the predetermined shape corresponding to the generally linear shaped portion of a vessel in which the device is to be disposed.

In one embodiment, the tubular body extends along a body lumen. In a second embodiment, the tubular body extends along the aorta. In a third embodiment, the tubular body extends along the aorta and into one iliac.

In a further embodiment, the intraluminal device is a graft for bridging an aneurysm in an artery of a patient.

In another embodiment, the tubular body may be tapered to allow for change in the diameter of the vessel in which the device is disposed.

In another embodiment, the tubular body may have variations in diameter along its length to allow for change in the diameter of the vessel in which the device is disposed.

In a still further embodiment of the invention the length of the tubular graft body is made from a single piece of material. The ends of this material may be straight, or shaped.

In a still further embodiment of the invention, the shape of the vessel or vessel portion in which the device is to be disposed may be pre-determined and the device chosen or specifically manufactured such that the shape of the device corresponds with the shape of the vessel or vessel portion. The shape of the vessel or vessel portion may, in preferred embodiments, be determined by either ultrasound, plain abdominal films or by CT scanning. In this manner, the device is custom made from imaging of the vessel or vessel portion such that it fits securely within the vessel or vessel portion.

In a second aspect, the present invention consists in an intraluminal device comprising a tubular graft body having a length, a first end and second end, and a supporting undulating wire, wherein the graft material towards at least one of the ends is scooped out or scalloped between each projecting crest of the wire. This reduces the possibility that a piece of the graft between those crests could project into the arterial lumen and partially occlude it or direct blood around the outside of the graft.

In a third aspect, the invention relates to the method for positioning an intraluminal device according to the present invention, including the steps of introducing a catheter or other delivery device into a vein, artery or other vessel in the body of a patient when the device body is in a radially compressed state; causing the intraluminal device to be moved through the catheter or other delivery device until the intraluminal device extends into the vessel from a proximal end of the catheter or other delivery device; causing or allowing the intraluminal device to expand; and withdrawing the catheter or other deliver device along with any other apparatus used to introduce the intraluminal device into the vessel.

In yet further embodiments of the invention for use in the treatment of aneurysmal disease, the wires described above may be held in place by sutures or adhesives or may be sandwiched between layers of a multi-layered tubular device body. In each of the foregoing embodiments, the wires are preferably disposed substantially within the device body. It is within the ambit of the invention, however, that the wires may alternatively be connected to, and disposed upon, the outer surface of the device body.

Likewise, supra renal fixation structures, including self-expanding barred wireforms and radiographic markers, tapers, and the teachings of applicants' expressly incorporated patents and serial numbers are contemplated as integral to the teachings of the present invention.

The intraluminal device according to this invention may be used in the treatment of aneurysms or stenotic disease. In addition to treating aortic aneurysms the device is particularly suitable for treating aneurysms of the arteries such as the renal and mesenteric arteries, the iliac artery and the subclavian artery. Further, in addition to the treatment of stenotic lesions in the peripheral vasculature, the invention may be used in the treatment of, inter alia, vessels comprising the coronary circulation. However, the application of the invention for use in the treatment of stenotic disease is not to be understood as limited to the vascular system only. To the contrary, the device may be used to treat stenotic lesions in other vessels including, but not limited to, those comprising the hepato-biliary and genito-urinary tracts.

In cases where the present invention is to be used for the treatment of stenotic disease, the wires are preferably formed of a thin biocompatible material such as Nitinol (a nickel titanium alloy, hereinafter "Nitinol"), stainless steel, tantalum, or ELGILOY (American Gage & Machine Company, Illinois, hereinafter "Elgiloy") (a cobalt-chromium-nickel alloy). The wires may be bare or may be coated with material having an elastic property such that the coating material covers the device body in both its radially compressed and radially expanded states. In preferred embodiments of the present invention for use in the treatment of stenotic disease, the device body may be formed from other suitable biocompatible materials, selected, for best results, on the basis of the material's capacity to withstand the compressive forces of the stenotic lesion and maintain patency of the vessel throughout the life of the device.

In cases where the invention is to be used for the treatment of aneurysmal disease, the tubular device body is preferably formed of a thin, biocompatible material such as Dacron® (E.I. du Pont de Nemours and Company, Wilmington, Del.) or polytetrafluoroethylene (PTFE) and/or combinations thereof The tube material may be crimped along its length to increase the flexibility of the device. However, uncrimped material may also be used when appropriate. In preferred embodiments of the invention for use in the treatment of aneurysmal disease, the device body may be formed from a material having a limited amount of diametric elasticity to ensure that it can be expanded into contact with the vessel wall, forming a seal between the wall of the device and the wall of the vessel such that the escape of the vessel contents into the aneurysmal sac is prevented.

In addition, in a further preferred embodiment, the device of the present invention includes a stent or a series of spaced apart stents which forms a framework which may be attached to an endoluminal graft. The framework of the device body may be circumferentially reinforced along its length by a plurality of separate, spaced-apart, malleable wires. Each of such wires can have a generally closed sinusoidal or zig-zag shape, also referred to as an "undulating" shape. The wires are preferably formed of stainless steel, another metal, or a plactic which is malleable and biocompatible. Alternatively, the wires may be made from a nickel-titanium alloy such as Nitinol, or other shape memory or heat sensitive material such that when the device is in situ within a vessel, the temperature in the vessel causes the material to take on a predetermined configuration. Such configuration may include a predetermined internal radius that is compatible with the vessel's internal radius, for example.

Each wire is preferably woven into the fabric of the device body to integrate the body and the reinforcing wires. This prevents any possibility of the wire reinforcement separating from the device body during introduction of the device, or throughout its life. If the device body is of a woven material, the wires may be interwoven with the device body by its manufacture. If the device body is not woven but is knitted or of an impervious sheet material, then the wires may be threaded through suitable holes formed in the device body. Alternatively, the stent or stents may be continuous and may be on the radially inner or the radially outer side of the graft wall. In either case, expansion of the stent or stents will cause the graft to expand and press against the wall of the vessel into which the device has been placed. In one particular embodiment of the invention, the wires are adapted such that substantially the entire periphery of the ends of the tubular body is reinforced.

The tubular stent or stents may be of the self-expandable type wherein the wires are made from a shape memory or heat sensitive material. In this embodiment, the tubular graft body is ejected from the proximal end of the catheter and into the target vessel. Once in the vessel, the tubular graft body takes on its pre-determined shape. Alternatively, the tubular graft body may be compressed within the lumen of a catheter such that upon release of the tubular graft body from the proximal end of the catheter and into the target vessel, the tubular graft body springs into its pre-determined shape. In a further embodiment, the expansion of the tubular graft body within the target vessel may be aided by way of a balloon which pushes the tubular graft body towards the wall of the target vessel when inflated.

The methods described herein for causing the expansion of the device body from a radially compressed state to a radially expanded state are by no means representative of an exhaustive list. Many alternative methods including, but not limited to, the use of electromagnetic fields and electric currents are well within the scope of the invention.

In addition to, or instead of being circumferentially reinforced, the tubular graft body may be longitudinally reinforced. In one embodiment, a longitudinally reinforcing wire may be connected to one or more circumferentially reinforcing wires. The advantage of longitudinal reinforcement is that the tubular graft body is less likely to compress along its length during placement of the tubular graft body in the target vessel. Such compression results in a concertina effect.

In as still further embodiment, the device of the invention may have a generally constant diameter along its length. Alternatively, the device may be frusta-conical in shape, with a diameter that increases or decreases along the length of the device.

In a further embodiment, the present invention consists of an intraluminal device comprising a tubular body having two ends which is capable of expanding or being expanded from a radially compressed state to a radially expanded state, and at least a plurality of engagement members being connected to or integral with a wall of the device body at a position located between the ends of the device body, the connection between the engagement member and the device body being such that the engagement member may occupy a first angular relationship with an adjoining part of the device body when the device body is radially compressed and a second and different angular relationship with an adjoining part of the device body when the device body is radially expanded. The engagement members, which are sometimes referred to as protruding portions or "crimps," engage the wall of a vessel lumen to inhibit longitudinal movement of the device therein. The wireform crimps may include sleeves over their tail segments and wire ends extending past the sleeves, directly engaging inside surfaces of body lumens.

In cases where "mechanically-aided change" is the method for causing the engagement members to change from their first angular relationship to a second angular relationship, a balloon may be used to cause such change. Such balloon may therefore be specifically preshaped to suit the particular device with which it will be used. Alternatively, however, the balloon to be used may not require any specific manufacturing arrangements that are out of the ordinary. Where the balloon is preshaped, it may be manufactured such that when inflated it has a series of dimples, between each of which the surface of the balloon does not bulge out as far as it does where the dimples are located. The dimples may be strategically located such that they will push respective engagement members into their second angular relationship when the device is introduced into the body of a patient.

The process of "mechanically-aided change" may be induced by a screw jack or other mechanical means that is introduced through the catheter or other delivery device along with the intraluminal device.

Where "heat-aided change" is the method for causing the engagement members to change from a first angular relationship to a second angular relationship, such change does not require specific intervention by the surgeon. In that case, the engagement members, upon the invention being introduced into the body of a patient, will undergo an increase in temperature caused by placement within the body of the patient, and will consequently change their angular relationship such that they acquire a second angular relationship with an adjoining part of the device body as compared to the first. In embodiments of the invention wherein "heat-aided change" is employed, materials such as Nitinol are preferably used in the manufacture of the engagement members.

In alternate embodiments of the present invention, wherein "heat-aided change" is used to change the angular relationships of the engagement members, it is possible to infuse the device with a heated liquid just prior to, or after, placement of the device in the vessel. This obviates the need to rely on body heat alone to induce "heat-aided change" of the engagement members. For instance, the device may be placed in a vessel yet the change in the relative position of the engagement members may be actuated at a later time. Thus, if the device showed signs of moving in the vessel, it may be secured in position by infusing into the vessel a liquid at a temperature above body temperature sufficient to cause the engagement members to change into their second relative positions.

Where "spring-aided change" is the method for causing the angular relationship of the engagement members to change, particular methods for positioning the device may be employed. In preferred embodiments of the invention where "spring-aided change" is employed, the engagement members are manufactured from a material, such as stainless steel, which has the ability to "memorize" its manufactured shape. Such materials have a tendency to return to their manufactured shape following events that cause the material to be temporarily deformed. Thus, a device using "spring-aided change" to cause the engagement members to change from a first angular relationship to a second angular relationship will be manufactured such that the engagement members are initially in the second angular relationship position. In preferred embodiments of the invention where "spring-aided change" is used, the method for positioning such a device involves: introducing a catheter into a selected vessel; manually compressing the engagement members into their first angular relationship positions such that in combination with the device body the invention has the smallest possible radial diameter along its length; inserting the device with the engagement members maintained in their first angular relationship positions into the catheter; causing the device to be carried through the catheter until the device extends into the vessel from the proximal end of the catheter, thereby enabling the engagement members to "spring" back into their respective second angular relationship positions (having been released from the confines of the catheter lumen or other similar instrument which had been maintaining the engagement members in their first angular relationship positions); and withdrawing the catheter along with any other apparatus used to introduce the device into the vessel.

Where "geometry-aided change" is the method for causing the engagement members to change from a first angular relationship position to a second angular relationship position, the construction of the invention is of particular relevance. In such embodiments, there is a physical relationship between the expansion of the device body (from a radially compressed state to a radially expanded state) and the change in angular relationship of the engagement members (from a first to a second angular relationship). That is, the change in the geometry of the device body as it expands causes the engagement members to change from their first angular relationship to a second angular relationship.

As is the case with the expansion of the device body from a radially compressed state to a radially expanded state, the methods described above for causing the engagement members to change from a first angular relationship to a second angular relationship are by no means representative of an exhaustive list. Many alternative methods, including the use of electromagnetic fields and electric currents are within the scope of the present invention.

Having occupied their respective second angular relationships, the engagement members will come into contact with the vessel wall and by so doing, provide resistance to any tendency for longitudinal migration of the device body through the lumen. Since perforation of the lumen is least desirable, the device of the present invention most preferably only engages the wall without causing substantial tissue damage.

In embodiments of the invention wherein at least one of the engagement members remains within the lumen of the device body once in its second angular position, the engagement member may act as a means for engaging other instruments or devices at any state throughout the life of the invention.

In another embodiment, the device of the invention may be extended through use of a supplemental graft. In this embodiment, the device is first placed within the vessel at the desired location. A supplemental graft may then be introduced through subsidiary arteries and overlapped with the lumen of the bifurcated part of the primary graft.

In a further embodiment, the exterior surface of the graft is 'texturized.' Such texture may be created through the presence of floaters. The floaters are formed during the weaving process by adding fibers lying along the warp of the weave. These additional fibers are partially integrated into the weave of the graft material. That is, each additional fiber skips one or more of the perpendicular fibers by not alternatively extending over, and under, adjacent perpendicular fibers. In this manner, sections of the floater fibers are woven into, and integrated with, the graft material, and sections of the floater fibers lie along the exterior of the graft surface.

The floater fibers may be positioned over the entire exterior surface of the graft or at selected locations on the graft. For example, the floaters may form 'cuffs' around the proximal and distal ends of the graft. Alternatively, the floaters may be placed in a geometric pattern. By way of example, and not of limitation, the floaters may be arranged in straight lines, angled lines, spaced-apart groups or patterns. The tension of each floater fiber may be selected by the manufacturer of the graft material during the weaving process. In this manner, the floaters may be loose or relatively taut against the graft surface. That is, the floaters may either loosely extend from the graft surface, or be tightly laid along the surface.

The intraluminal device according to this invention may be used in the treatment of aneurysms or stenotic disease. In addition to treating aortic aneurysms, the device is particularly suitable for treating aneurysms of the femoral artery, the popliteal artery, the thoracic segment of the aorta, visceral arteries such as the renal and mesenteric arteries, the iliac artery and the sub-clavian artery. Further, in addition to the treatment of stenotic lesions in the peripheral vasculature, the invention may be used in the treatment of, inter alia, vessels comprising the coronary circulation. The application of the invention for use in the treatment of stenotic disease is not to be understood as limited to the vascular system only, the device may be used to treat stenotic lesions in other vessels including, for example, those comprising the hepato-biliary and genito-urinary tracts.

BRIEF DESCRIPTION OF THE DRAWINGS

The present invention is now described with reference to the accompanying drawings, wherein like numbers represent like portions.

DETAILED DESCRIPTION

The present invention provides a novel way to enhance the human vasculature, as well as other vessels, by means of grafts which have a generally linear, predetermined shape for specific applications. Unlike known systems, the instant teachings may be used to ameliorate problems in vessels having particularly difficult anatomical structures. For example, the instant invention may be used in a patient having atypical anatomy. Such a situation may arise if the patient's aorta is unusually elongated, or if the aorta does not clearly branch into the first and second iliacs. The present invention is also particularly suited for patient's having one totally occluded iliac, or for patients whose own prosthesis is failing. In the latter capacity, the present invention may be used as a conversion graft, or to supplement a failed or failing graft.

In the past, medical professionals have treated patients having a need for a graft to patch a generally straight vessel with a modified bifurcated graft. To use a bifurcated graft in such a patient, the medical professional would typically sew or otherwise close one "leg" of the graft. The present invention obviates the need for this additional step, and provides an even flow path for the blood as it passes through the graft. The present invention thus reduces the risk and incidence of thrombus formation.

Figure 1:
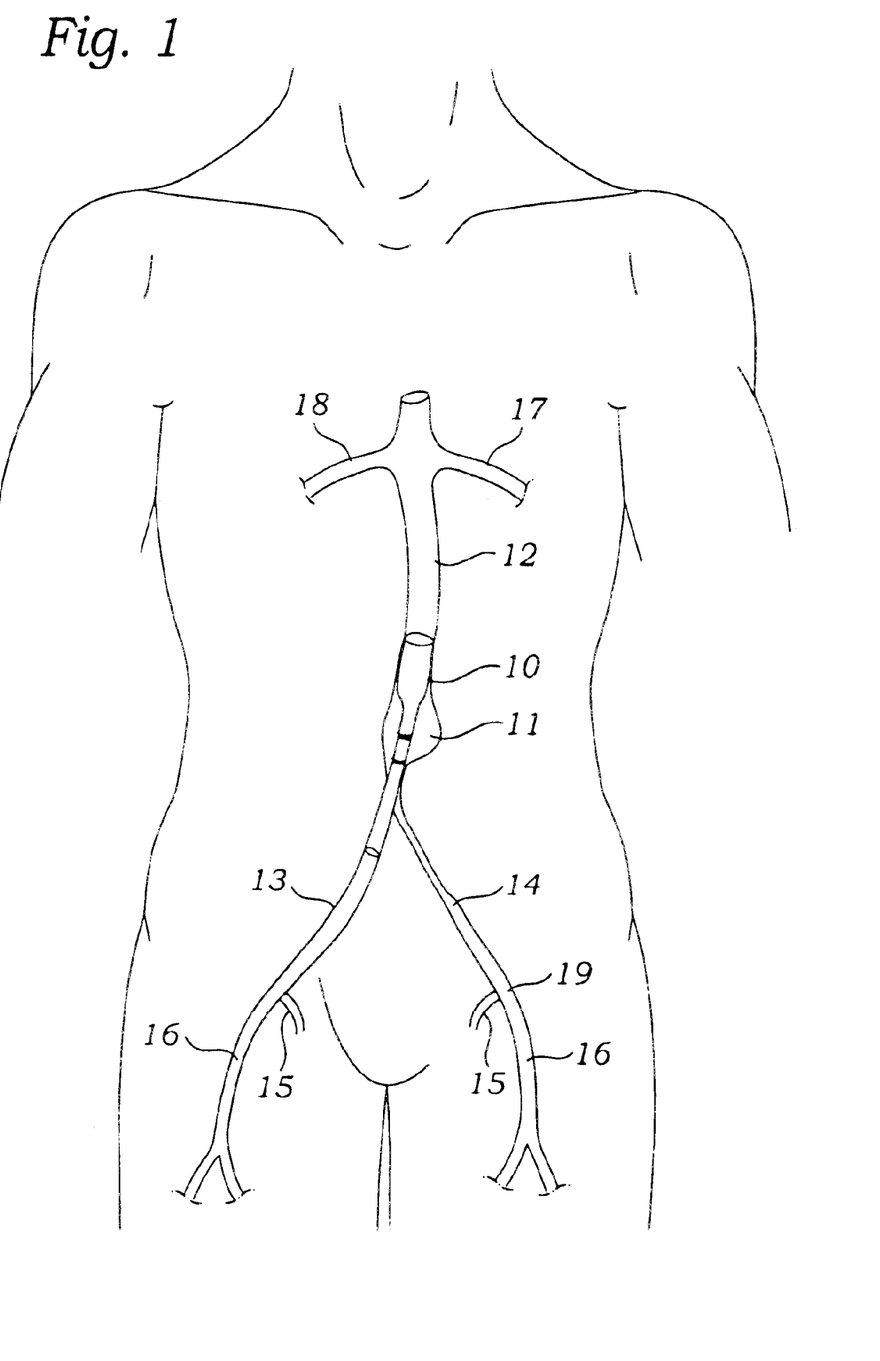
FIG. 1 is a diagrammatic partially cut-away ventral view of a patient with an aortic aneurysm, and one completely occluded iliac, which as been bridged by a device according to one embodiment of the present invention.

FIG. 1 is a diagrammatic partially cut-away ventral view of a patient with an aortic aneurysm, and one completely occluded iliac, which as been bridged by a device according to one embodiment of the present invention. The endovascular graft 10 is adapted for insertion transfemorally into a patient to achieve bridging and occlusion of a aneurysm 11 present in an aorta 12. While the invention will be described herein as suitable primarily within an aorta or other blood vessel, one skilled in the art will realize that the present invention has wide applicability and may be used in many vessels other than the aorta.

As shown in FIG. 1, the aorta 12 in a patient having typical anatomy bifurcates to form the common iliac arteries 13 and 14. In the patient shown in FIG. 1, one iliac has become completely occluded, so no blood may flow through it. As such, emplacement of the graft 10 will not interfere with blood flow into the second iliac 14. The aortic aneurysm is located between the renal arteries 17 and 18 and the junctions of the bifurcation of the aorta 12 into the common iliac arteries 13 and 14. The common iliac arteries typically divide into the external 19 and internal 15 iliac arteries. The external iliac artery 19 eventually becomes the femoral artery 16, through which the graft is typically inserted into the patient.

Figure 2:
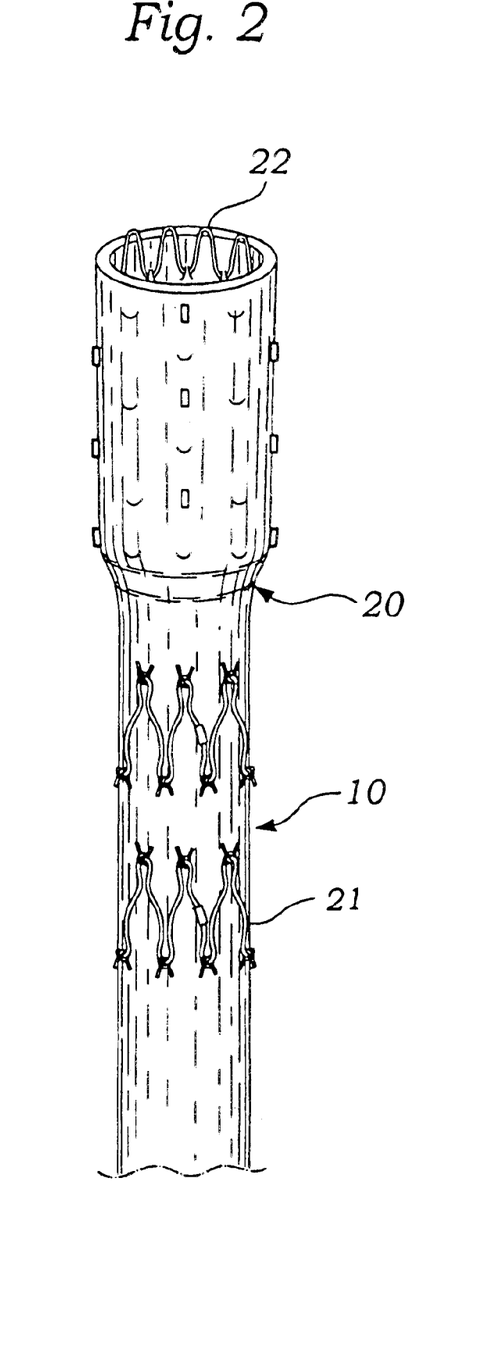
FIG. 2 is a simplified view of a device according to one embodiment of the present invention.

FIG. 2 is a simplified view of a device according to one embodiment of the present invention. As shown in FIG. 2, the graft 10 may vary in diameter. Such variations in diameter are preferably accomplished by tapering, such as the tapering shown at 20. While only one change in diameter is shown in FIG. 2, it should be realized by one skilled in the art that the graft 10 may also vary in diameter at two or more locations. Such variations may include expansions in diameter, as well as reductions.

In use, the shape of the vessel into which the device is to be disposed may be imaged and the device chosen or specifically manufactured such that the shape of the graft 10 corresponds with the shape of the vessel. Imaging may be by way of ultrasound, plain abdominal films or by CT scanning. In this manner, the shape of graft 10 is selectively chosen so that the graft 10 fits securely within the vessel.

The graft 10 is equipped with a plurality of undulating, supporting exterior wireforms 21 and interior wireforms 22. These wireforms 21 and 22 may be self-expanding or balloon expandable. The wireforms may be designed such that the self-expansion occurs when the wireform is at body temperature and unconstrained. In the embodiment of the present invention having balloon-expandable wireforms, such wireforms are preferably at least partially formed of a malleable material which is initially formed in a radially compact configuration, and is plastically deformable to achieve a radially expanded configuration. The graft 10 may be designed to include only balloon-expanding or self-expanding wireforms. Alternatively, self-expanding and balloon-expanding wireforms may be both included within the same graft 10. Such use of both self-expanding and balloon-expanding wireforms may be desirable, for example, when the professional who is deploying the device wishes to set a first portion before deploying the entire graft.

Figure 3A:
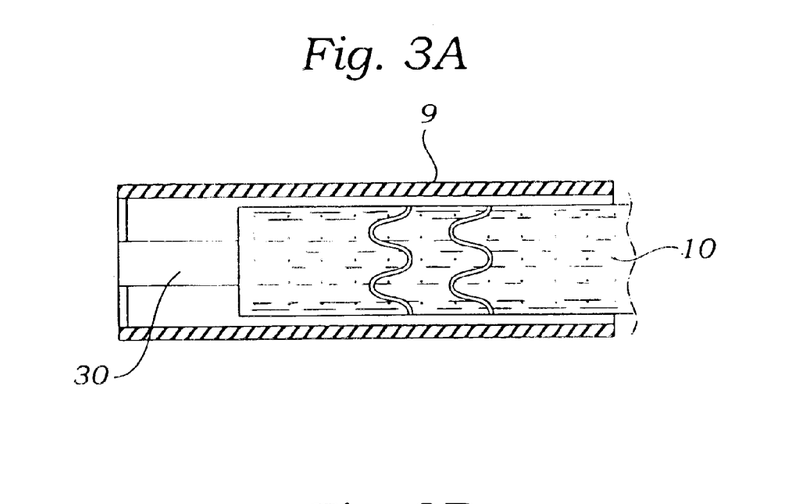
FIGS. 3a and 3b are simplified representations of a delivery mechanism of one embodiment of the present invention.
Figure 3B:
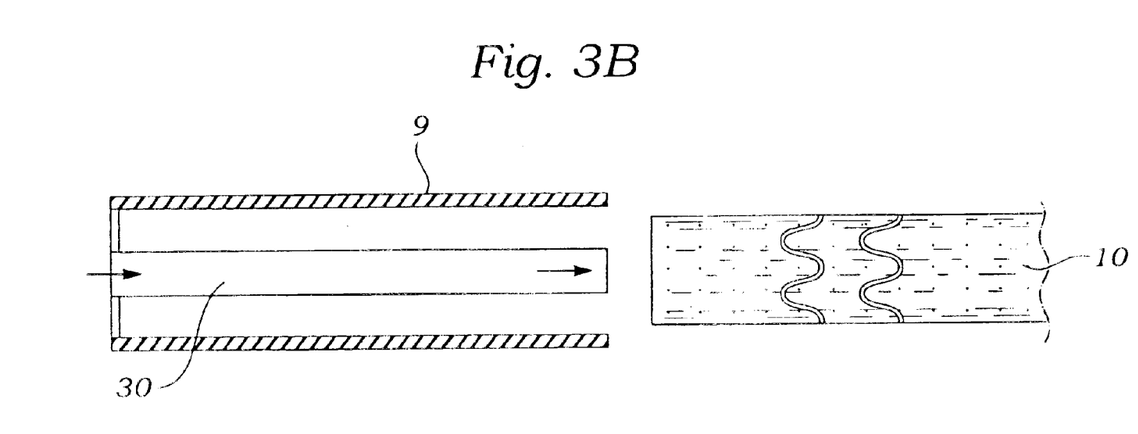

FIGS. 3a and 3b are simplified representations of a delivery mechanism of one embodiment of the present invention. As shown in FIGS. 3a and 3b, the graft 10 may be introduced into the aorta 12 through the use of a catheter 9. During such a procedure, the graft 10 is inserted inside the catheter 9 and introduced into one of the femoral arteries 16 of the patient. Once the catheter 9 is located appropriately with its proximal end in the aorta 12, the graft 10 is ejected from the catheter and expanded (or allowed to expand) such that each end of the graft 10 is in intimate contact around its full periphery with the aorta 12. So placed, the graft 10 bridges the aneurysm 11 and isolates any thrombosis or gelatinous material associated with the aneurysm between the exterior of the graft and the vessel wall 10 to reduce the risk of embolisation.

Figure 4:
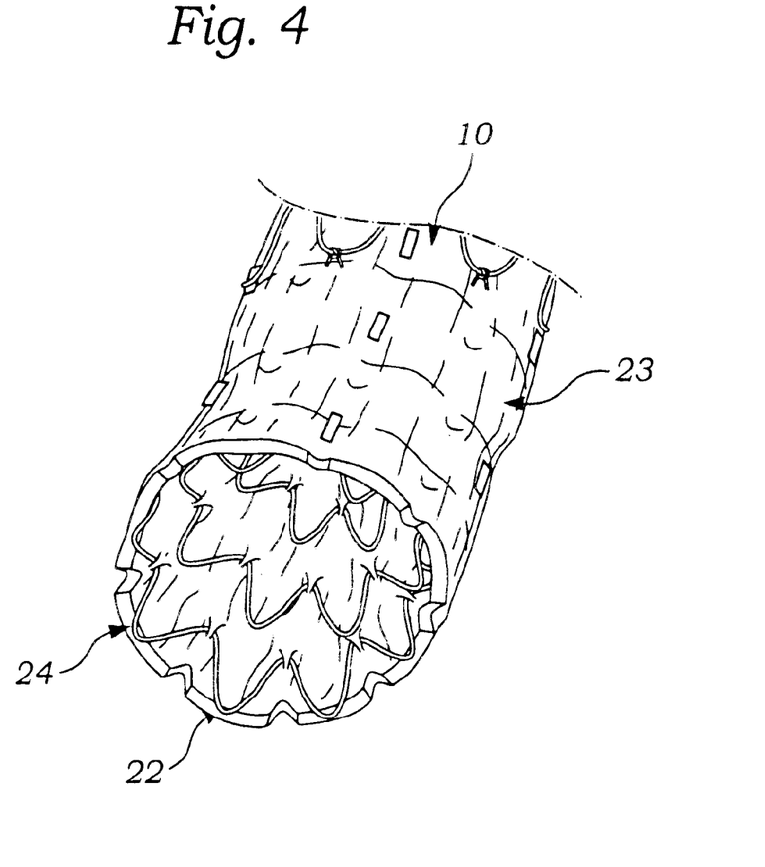
FIG. 4 is a perspective view of one end of a device according to one embodiment of the present invention.

FIG. 4 is a perspective view of one end of a graft 10 according to one embodiment of the present invention. The graft 10 includes a generally cylindrical tube 23 of graft material. Such tube 23 may be formed of a material such as Dacron®, for example. The tube 23 is reinforced along its length with a plurality of separate spaced-apart wireforms 22 that are interwoven in the Dacron®. That is, certain portions of the wireforms extend through the tube 23 as the wireform proceeds around the circumference of the tube 23. As shown in FIG. 4, the wireforms may be configured to undulate in a generally sinusoidal manner. If the tube 23 is made from one layer of material, as shown in FIG. 4, the wireforms may extend through the Dacron®, and be seen on the exterior of the tube 23. Alternatively, the graft 10 may include a plurality of layers of graft material (not shown). In such a graft, the wireforms will not necessarily be seen on the exterior of the graft 10 body.

As shown in the embodiment of the present invention depicted in FIG. 4, the end 24 of the graft 10 is scooped out or scalloped between each projecting crest of the wireform 22. Such a configuration may reduce the possibility that a piece of the tube 23 between those crests could project into the arterial lumen and partially occlude it, or direct blood around the outside of the graft.

Figure 5:
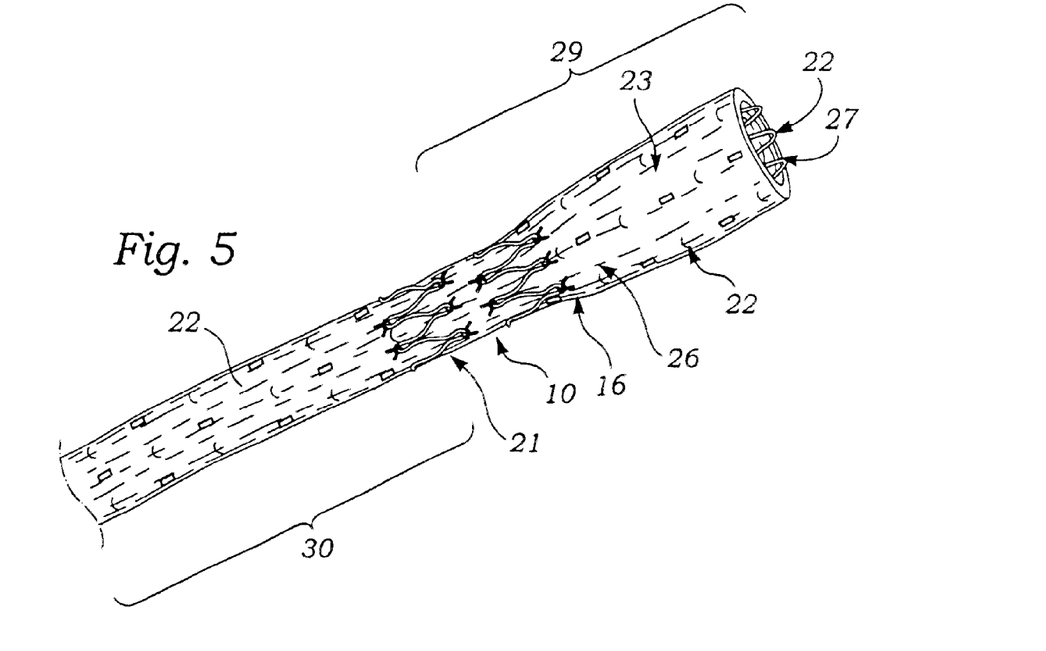
FIG. 5 is a perspective view of a device according to one embodiment of the present invention.

FIG. 5 is a perspective view of a graft according to one embodiment of the present invention. The graft 10 is comprised of a generally cylindrical tube 23 of a material such as Dacron®. As shown in FIG. 5, this tube 23 may be tapered so as to achieve a better fit within the vessel. Wireforms 22 as described above may be seen extending through the tube 23. The graft 10 is also equipped with a plurality of protruding portions 26. These protruding portions 26 may be designed to selectively engage the vessel wall, and inhibit migration of the graft within the vessel.

As shown in FIG. 5, the end 27 of the graft 10 is generally straight as opposed to scalloped. Depending on the condition and configuration of the vasculature of the patient, such a configuration may be preferred. The end 27 may be formed such that it is generally perpendicular to the length of the graft 10. Alternatively, the end 27 may be formed such that it lies at an angle to the length of the graft 10.

In the embodiment of the present invention shown in FIG. 5, the graft 10 is composed of a first section 29 and a second section, or extension, 30. To implant such a graft 10 in a vessel, the first section 29 is first positioned and expanded (or allowed to expand). The second section is then positioned within the vessel so as to engage both the first graft and the vessel wall when expanded. If desired for the particular anatomy involved, and particularly when used to repair or reinforce an existing graft, however, it is often the case that the graft is effectively lodged solely within the primary graft and not required to impact the vessel wall.

Such implantation of the first section 29 and second section 30 may be achieved through use of a catheter system. Such system may include one catheter configured to deploy both sections, or may include a plurality of catheters, each inserting a selected section.

Figure 6:
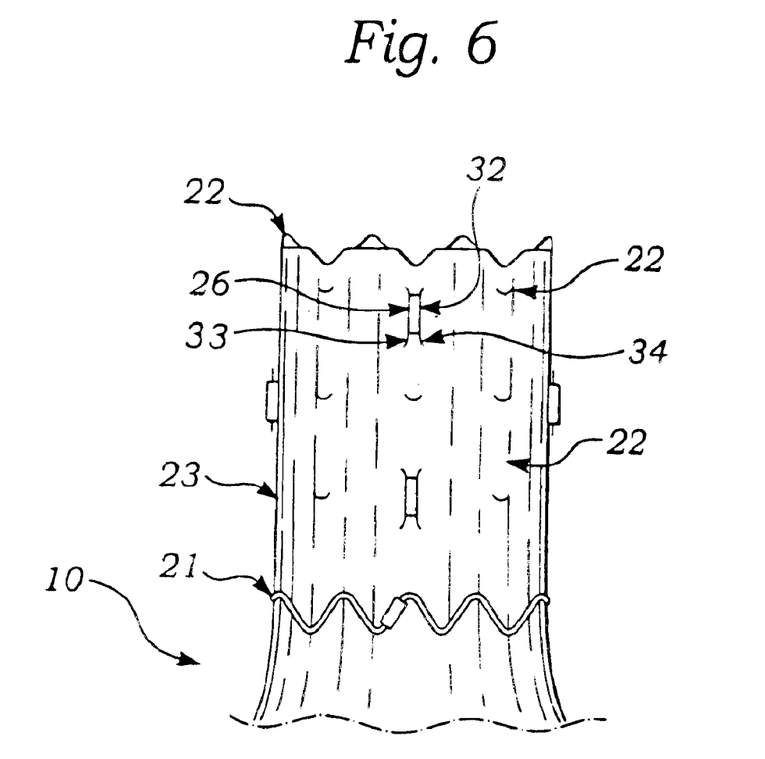
FIG. 6 is a perspective view of a device according to one embodiment of the present invention.

FIG. 6 is a perspective view of a device according to one embodiment of the present invention, in which the engagement members, or protruding portions 26, may be easily seen. In this embodiment of the present invention, the protruding portions 26 are formed from crimps 32 extending around a first end 33 of a first wireform 22, and a second end 34 of a second wireform 22. The stents in this embodiment of the present invention may each be formed from a plurality of wireforms together extend around the circumference of the graft. For example, in the situation where two wireforms together formed one turn around the circumference of the graft, each would extend through 180°. Where the ends of each wireform meet, they extend through the graft so that they may be crimped together.

In a further embodiment of the present invention, as shown in FIG. 6, the ends of the wireforms may extend past the area where the ends of two wireforms are either joined or held together. In this embodiment, the ends of the wireforms are particularly suited to engage the vessel wall. These protruding portions 26, which should be so designed such that the ends of the wireforms do not pierce the vessel wall, or impact harmfully upon the intima of lumens to any significant extent, serve to maximize the stability of the graft.

As noted above, there are at least four preferred mechanisms whereby the protruding portions 26 may change from having a first angular relationship with an adjoining part of a wall of the device body to having a second angular relationship with an adjoining part of the wall of the device body. These are: (1) change of angular relationship effected by the physical force of an inflating balloon or other mechanical device ("mechanically-aided change"); (2) self-change following the introduction of the invention into the body of a patient, wherein a patient's body temperature causes the temperature of the engagement members to rise, thereby enabling the engagement members to change from their first angular relationship to their second angular relationship ("heat-aided change"); (3) self-change following deployment of the invention from the catheter or similar device used to introduce the invention into the body of a patient, wherein a property of the material comprising the engagement members is a "memory" of a preferred second angular relationship position, such that the engagement members may "spring" into that position upon release from the catheter or similar device ("spring-aided change"); and, (4) change of angular relationship effected by the change in the geometry of the device body as it expands from a radially compressed state to a radially expanded state ("geometry-aided change").

Figure 7:
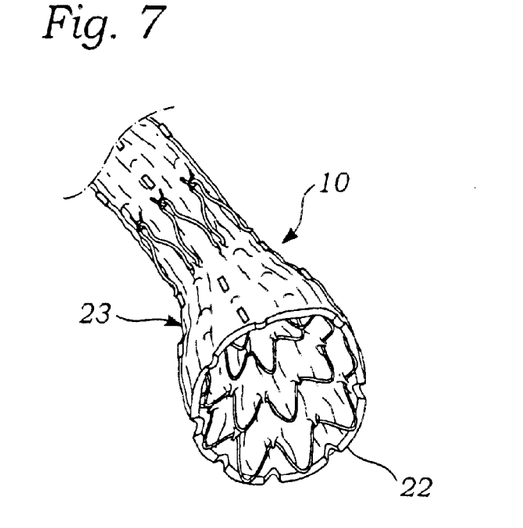
FIG. 7 is a perspective view of a device according to one embodiment of the present invention.

Referring now to FIG. 7, an alternate preferred embodiment shows a self-expanding or balloon expandable graft 10 utilizing, for example, a Dacron® material for the tube 23 forming the graft body. According to the instant teachings, a graft may be secured to a desired portion of the aorta and iliac arteries by use of the self-expanding radial force of wireforms attached to the Dacron® graft. According to this teaching, a graft having at least 28 mm of trunk may include a tapered portion. Balloon attachment or self-expansion may be used according to this alternate embodiment, as discussed above and claimed below.

While the foregoing is a complete description of the preferred embodiments of the invention, various alternatives, modifications, and equivalents may be used. Moreover, it will be obvious that certain other modifications may be practiced within the scope of the appended claims. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. An intraluminal device for placement in a living body vessel comprising:

a tubular body having a linear shape and an inner and an outer surface, the tubular body being radially expandable from a compressed state to an expanded state;

a plurality of undulating filaments extending circumferentially about the tubular body and forming a generally ring-shaped configuration; and a plurality of specifically-configured engagement members disposed on the outer longitudinal surface of the tubular body and configured to frictionally engage an inner wall of a body vessel so as to inhibit longitudinal movement of the tubular body without piercing the vessel wall.

2. The intraluminal device as in claim 1, wherein the tubular body is comprised of first and second tubular portions.

3. The intraluminal device as in claim 1, wherein each filament has a first and a second end extending through the tubular body and forming an abutting junction between two filaments.

4. The intraluminal device as in claim 1, wherein select ones of the filaments lie along the inner surface of the tubular body.

5. The intraluminal device as in claim 1, wherein the filaments are woven through the tubular body.

6. The intraluminal device as in claim 1, wherein said plurality of engagement members are constructed of a biocompatible, malleable material.

7. The intraluminal device as in claim 1, wherein said plurality of engagement members are constructed from a material selected from the group consisting of a cobalt-chromium-nickel alloy, a nickel-titanium alloy, stainless steel, plastic, and tentalum.

8. The intraluminal device as in claim 1, wherein the plurality of engagement members are disposed on the outer surface of said device in a fixed geometric pattern.

9. The intraluminal device as in claim 8, further including a self-expanding stent portion circumferentially disposed along the outer surface and towards an end of the tubular body.

10. The intraluminal device as in claim 1, wherein each engagement member is formed by a joining member securing the junction between the two filaments.

11. The intraluminal device as in claim 10, wherein the filament are wires each having tail segment, and the joining member is a sleeve crimped over the tail segments.

12. The intraluminal device as in claim 11, wherein the tail segments extend past the sleeves.

13. The intraluminal device as in claim 11, wherein each wire extends approximately 180° around the circumference of the tubular body and the tail segments join with a like wire in two locations to form two engagement members.

14. The intraluminal device as in claim 11, wherein the wires are preferably formed of a thin biocompatible material selected from the group consisting of:

Nitinol;

stainless steel;

tantalum, and

Elgiloy.

15. The intraluminal device as in claim 1, wherein said device is an aorto-uniliac stent-graft.

16. The intraluminal device as in claim 1, wherein the engagement members are connected to the tubular body such that each engagement member lies in a first angular relationship with the tubular body when in its compressed state, and a second, different angular relationship with the tubular body when in its expanded state.

17. The intraluminal device as in claim 16, wherein the longitudinal wire connects to at least one of the undulating filaments extending circumferentially about the tubular body.

18. The intraluminal device as in claim 1, wherein the engagement members are made of a spring material such that each engagement member lies in a first angular relationship with the tubular body when in its compressed state and when restrained from outward expansion, and a springs outward to second, different angular relationship with the tubular body when unrestrained.

19. The intraluminal device as in claim 1, wherein the engagement members are made of a material that changes shape upon a temperature change such that each engagement member lies in a first angular relationship with the tubular body prior to placement in the living body vessel, and a second, different angular relationship with the tubular body when placed in the living body vessel.

20. The intraluminal device as in claim 1, wherein the engagement members are made of a material that changes shape upon a temperature change such that each engagement member lies in a first angular relationship with the tubular body prior to and after placement in the living body vessel, and a second, different angular relationship with the tubular body when exposed to a temperature above body temperature.

21. The intraluminal device as in claim 1, wherein the engagement members are made of a material that changes shape upon application of an excitation selected from the group consisting of:

an electromagnetic field; and an electric current.

22. The intraluminal device as in claim 1, wherein the tubular body comprises a knitted or impervious material and includes holes, the filaments being threaded though the holes to couple with the tubular body.

23. The intraluminal device as in claim 1, wherein the tubular body is longitudinally reinforced with at least one longitudinal wire.

24. An endoluminal graft for placement in a living body vessel comprising:

an unbranched pliable, tubular graft body having a predetermined linear shape and circumference, an interior surface and an exterior surface; and a plurality of generally circular wireforms circumferentially disposed along the interior surface of said graft body, said wireforms each being composed of at least two undulating wires, a first wireform being joined to a second wireform to form a joined pair of wire ends, each pair of wire ends extending through the graft body to the exterior surface thereof such that there is relative movement between the graft body and the wire ends, wherein the wire ends define a projection extension configured to frictionally engage a wall of the body vessel.

25. The endoluminal graft as in claim 24, further including self-expanding stent portion circumferentially disposed along the exterior surface and towards an end of the graft body.

26. The endoluminal graft as in claim 24, wherein said pliable, tubular graft body is expandable from a first radially compressed configuration to a second expanded configuration;

wherein the wire ends are joined together by means of a sleeve, a portion of said wire ends extending beyond said sleeve so as to define a projection extension;

and further wherein said sleeve remains substantially parallel to said graft before, during and following deployment.

27. An intraluminal conversion graft comprising:

a main trunk portion defining an interwoven tubular stent and graft element having at least a plurality of wireforms disposed therethrough;

engagement means for attaching a portion selected from the group consisting of a previously emplaced graft, a native vessel and an extension portion; and an extension portion adapted to mate with the main trunk portion within a diseased segment of vessel;

wherein said main trunk portion further comprising at least four balloon expandable wireforms in combination with at least a self-expanding wireform.

28. The conversion graft of claim 27, wherein each of said main trunk portion and said extension portion is tapered.

29. The conversion graft of claim 28, further comprising a supplemental means for enhancing tissue ingrowth and generation of a cellular matrix disposed upon an outer surface of said graft.

* * * * *